(12) United States Patent
Sutherland et al.

(10) Patent No.: US 7,070,767 B2
(45) Date of Patent: Jul. 4, 2006

(54) FOSSORIAL RODENT CONTROL COMPOSITIONS AND METHODS

(75) Inventors: Donald Sutherland, Glenbow Road, R.R. 2, Cochrane (CA) T4C 1A2; David Schmunk, 251212 Tower Ridge Estates, Calgary (CA) T3Z 2M2

(73) Assignees: Donald Sutherland, Cochrane (CA); David Schmunk, Calgary (CA)

(*) Notice: Subject to any disclaimer, the term of this patent is extended or adjusted under 35 U.S.C. 154(b) by 3 days.

(21) Appl. No.: 10/248,855

(22) Filed: Feb. 25, 2003

(65) Prior Publication Data

US 2003/0152604 A1 Aug. 14, 2003

Related U.S. Application Data

(60) Division of application No. 09/496,580, filed on Feb. 2, 2000, which is a continuation of application No. PCT/CA99/00667, filed on Jul. 22, 1999, now Pat. No. 6,558,684, which is a continuation-in-part of application No. 09/120,446, filed on Jul. 22, 1998, now abandoned.

(51) Int. Cl.
*A01N 25/16* (2006.01)
*A01N 65/00* (2006.01)
(52) U.S. Cl. .......................... 424/46; 424/405; 424/755
(58) Field of Classification Search .................. 424/43, 424/405, 755, 46
See application file for complete search history.

(56) References Cited

U.S. PATENT DOCUMENTS 4,330,086 A * 5/1982 Nysted ........................ 239/8
5,104,658 A * 4/1992 Hagarty ..................... 424/405

FOREIGN PATENT DOCUMENTS

WO 97/14309 * 4/1997

* cited by examiner

*Primary Examiner*—Neil S. Levy
(74) *Attorney, Agent, or Firm*—Bennett Jones LLP

(57) ABSTRACT

A method and composition for controlling fossorial rodents are disclosed. The composition is a mixture of water, a foaming agent and a respiratory irritant. The respiratory irritant is preferably finely ground white mustard seeds. The mixture is aerated through a nozzle and pumped into the rodent burrow to exterminate the resident rodent.

10 Claims, No Drawings

FOSSORIAL RODENT CONTROL COMPOSITIONS AND METHODS

CROSS REFERENCE TO RELATED APPLICATIONS

This application is a divisional application of U.S. patent application Ser. No. 09/496,580 U.S. Pat. No. 6,558,684 filed on Feb. 2, 2000, which is a continuation of PCT/CA99/00667, filed on Jul. 22, 1999 which was a continuation-in-part of U.S. patent application Ser. No. 09/120,446 filed on Jul. 22, 1998, now abandoned.

BACKGROUND OF INVENTION

The present invention relates to methods and compositions for the control and extermination of fossorial rodents.

Fossorial rodents include Richardson ground squirrels (*Spermophilus richardsonii*), commonly referred to as gophers, which are a destructive pest species throughout the prairie regions of North America. The burrowing and feeding activities of ground squirrels impact heavily on forage and grain crops. The burrows themselves create a physical hazard to horses, cattle, farm equipment and the unwary pedestrian. Other fossorial rodents such as Norway rats (*Ratus norvegicus*) and pocket gophers (Thomomys talpoides) are also considered pests. Norway rats in particular are difficult to control in both urban and rural settings.

Conventional methods for controlling ground squirrels include the use of poisoned bait, smoke bombs, water-flooding the burrow systems and even the physical removal of ground squirrels from their burrows using large vehicle mounted vacuum systems. Each of these prior art methods is unsatisfactory or ineffective for various reasons.

The use of strychnine and similar poisons is environmentally disadvantageous because of the danger posed to pets, predators and scavengers which may feed on the dead ground squirrels or the poisoned bait itself. These may include such valued species as hawks, eagles, owls, coyotes, badgers and the like. Because of this danger, there is Canadian legislation which limits the concentration of the poison which may be used, which limits the effectiveness of the poison. In mid-summer when food supplies for rodents are abundant, the effectiveness of baited poisons in dilute concentrations approaches nil.

Flooding burrow systems with water is rarely effective because the water never completely floods out the burrow; there are always anticlinal air pockets in the burrow system which allow the ground squirrels to survive until the water is absorbed into the ground. The vacuum systems are elaborate, labour intensive and expensive to operate.

Foam-based rodent control systems are known. In most cases, the foam is used as a carrier for a poison which is ingested by the rodent. In U.S. Pat. No. 3,816,610 issued to Lusby, a rigid or flexible foam plastic is used to carry a rodenticide. The foam is applied to block openings to a burrow or a hole in which the target rodent resides. It is intended that the rodent eat the foam to reopen the blocked opening and thereby ingest the poison.

Adhesive foams containing rodenticide have been used which stick to the rodent causing grooming behavior. This causes the rodenticide to be taken up orally.

In U.S. Pat. No. 3,473,252 issued to Kramer et al., a method of exterminating rats using foams comprising hardenable synthetic resins is disclosed. These foams are propelled into holes to envelop the rat and asphyxiate the rat by displacing air present in the hole. The foam then hardens into a permanent plastic which entombs the rat remains. The preferred foam disclosed is based on a urea formaldehyde synthetic resin which polymerizes to form the permanent foam. Urea formaldehyde foams are no longer used due to their potential harmful effects on humans. The other foams disclosed may not be economically used in this manner. The permanent nature of these foams have adverse effects on the environment when used in applications not involving building structures. As well, the dead animal remains cannot be buried or otherwise disposed of because of the permanent nature of the foam.

Therefore, there is a need in the art for a control system for ground squirrels and other rodents which mitigates the disadvantages of the prior art. In particular, there is a need for a control system which is humane, effective, non-toxic to livestock, predators, scavengers and pets and is environmentally friendly.

SUMMARY OF INVENTION

In one aspect of the invention, the invention comprises a method of exterminating burrowing animals, said method comprising the steps of passing a treatment composition comprising a foaming agent through an aerating nozzle down a burrow containing an animal such that the burrow is substantially filled with a non-persistent foam, thereby forcing the animal to inhale the foam. In the preferred embodiment, the treatment composition used in the method is biodegradable and further comprises a respiratory irritant. It has been found that the respiratory irritant is preferably finely ground seeds of plants of the genus *Brassica* (family Cruciferae), commonly referred to as mustard. In particular, ordinary mustard, also known as white or yellow mustard, is used. These seeds are from *Brassica alba* (also known as *Brassica hirta* or *Sinapis alba*) or white mustard.

In another aspect of the invention, the invention comprises a composition for use in the extermination of a burrowing animal resident in a burrow, said composition comprising a foaming agent and a respiratory irritant. In the preferred embodiment, the respiratory irritant is around mustard seed.

In another aspect of the invention, the invention comprises the use of a composition for asphyxiating a burrowing animal resident in a burrow, wherein said composition comprises a foaming agent and does not include a synthetic resin. In yet another aspect, the invention comprises the use of a non-persistent foam composition for asphyxiating a burrowing animal resident in a burrow.

The concentration of finely ground mustard in preferred embodiments of the invention is between about 0.3% and about 0.5% (w:v) when diluted and ready to use. The invention may be supplied in a concentrated form which is diluted with water to use level concentrations.

The foaming agent may be a liquid surfactant which forms a relatively stable and dense non-persistent foam when aerated. In the preferred embodiment, the foaming agent is a commercially available aqueous forest fire suppressant foam which is biodegradable.

DETAILED DESCRIPTION

The present invention has specific application to ground squirrels, pocket gophers, moles, rats and rabbits, which are all burrowing rodents. However, it is not intended to limit the application of this invention to these species. The methods and compositions disclosed herein may be readily adapted to control any unwanted burrowing animal by those skilled in the art and any such adaptations are intended to fall within the scope of the invention claimed herein.

In general terms, the preferred embodiment of the invention comprises a mixture of a liquid concentrate foaming agent and ground mustard seed. This mixture is used by combining it with water and aerating to create a foam which is introduced into the burrow to be treated. In an alternative embodiment, the foaming agent and ground mustard may be dry mixed before the addition of water or in a further alternative embodiment, may be prepared in a ready-to-use concentration.

Suitable foaming agents create a relatively dense non-persistent foam. As used herein, "foam" refers a mass of gaseous bubbles formed in a liquid. As used herein, "non-persistent" refers to the fact that the foam will remain fluid and eventually separate into its liquid and gaseous components. Foams which are not "non-persistent" will harden into a permanent foam where the gas bubbles are trapped in a substantially solid phase. Such foams include urea-formaldehyde, polyurethane or thermoplastic polymer based foams and are not intended to be used with the present invention.

Suitable foaming agents should create a non-persistent, relatively stable and dense foam upon aeration. The foam's function is to substantially fill the animal burrow, leaving no air pockets, such that the animal is forced to inhale the foam into its trachea and lungs. The foam should be dense enough to cause asphyxiation of the animal within a reasonable length of time and stable enough to remain in emulsion for that length of time. In the preferred embodiment, well known forest fire suppressant foams are used. Phos-Chek™ WD-881 manufactured and supplied by Astaris LLC (Ontario, Calif.) is satisfactory as well as Fire-Trol® FireFoam® manufactured and supplied by Fire-Trol Canada Company (formerly known as Chemonics Industries (Canada) Ltd.). The exact compositions of these foaming agents are trade secrets of their manufacturers; however, they are known to be a mixture of surfactants and other performance components dissolved in a water-miscible system. For example, Fire-Trol® FireFoam® is known to comprise salts of alkyl-sulfonic acids, hexylene glycol, alkanol I and alkanol II. Phos-Chek WD-881 is known to primarily comprise alpha-olefin sulfonate. Generic foaming agents such as ammonium deceth sulfate are also suitable for use with the present invention. Foam-creating surfactants are well-known to those skilled in the art and suitable foaming agents may be determined with minimal experimentation.

It is preferred that the foaming agent be biodegradable in order to minimize any adverse environmental impact. As used herein, "biodegradable" refers to substances capable of being decomposed by bacteria or other living organisms or spontaneous decomposition if left in a natural environment. Fire-Trol® FireFoam® and Phos-Chek WD-881 are both known to be practically non-toxic orally, with each having an LD50 of greater than 5.000 mg/kg in rats.

The specific foaming agents disclosed above are water-miscible agents and are therefore used with water as the carrier. It is readily appreciated that alternative foaming agents which are immiscible in water may be used and therefore, different appropriate carriers may be used in the place of water. However, water is the preferred carrier of the foaming agent and the mustard because it is ubiquitous, inexpensive and generally benign.

It is believed that the foam asphyxiates the rodents because it substantially fills the burrow, including all anticlinal pockets which would capture air pockets if the burrow were to be filled with water. In the preferred embodiment, it is believed that the ground mustard seed acts as a respiratory irritant which hastens the asphyxiation caused by the foam. The foam is likely irritating to the rodent's respiratory system, even in the dilute concentrations used in the preferred embodiment herein. It is known that the proprietary foaming agents disclosed above are irritating to human skin and mucosal membranes. In effect, it is believed that the foam fills the burrow completely and therefore forces the rodent to inhale the foam and the mustard which is dissolved and colloidally dispersed in the foam. As a result, the rodent is quickly asphyxiated by the combination of the foam and the mustard. It is believed that the mustard speeds up the asphyxiation by further irritating the respiratory epithelium of the respiratory tract and lungs or by causing gasping which causes the rodent to inhale the foam more deeply and in larger amounts.

Therefore, as used herein, "respiratory irritant" refers to (a) any substance which irritates the respiratory epithelium of the animals respiratory tract or lungs; (b) any substance which is shown to hasten the asphyxiation of an animal which inhales a combination of a non-persistent foam and the substance; or (c) any substance which causes the death of an animal which inhales the substance.

It is believed that the effective ingredient in the mustard is the mustard oil which forms when the mustard powder is contacted with water. Mustard oil is responsible for the "hot" taste of mustard. White mustard seeds contain the glucoside sinalbin, which is hydrolysed to produce mustard oil by the enzyme myrosinase, which is present in the mustard powder and which is activated by water. It is assumed that two other varieties of mustard seed, black mustard seeds from the mustard plant *Brassica nigra* a, and brown mustard from the mustard plant *Brassica juncea* contain similar glucosides and enzymes which also yield a mustard oil. Black mustard and brown mustard are generally more potent than white mustard and it is assumed that they may be used alternatively in the place of white mustard in the preferred embodiment of the present invention.

Of course, if it is determined that a certain compound contained in ground mustard, other than the mustard oil disclosed above, is the effective agent, that particular compound may be a preferred respiratory irritant for use with the present invention.

Mustard is the preferred respiratory irritant because it is effective in hastening the death of rodents which have inhaled the foam/mustard combination, it is non-toxic to humans and other wildlife species, is biodegradable and is otherwise environmentally innocuous. Furthermore, it is available in commercial quantities in a finely ground form which disperses quickly and evenly into the concentrated foaming agent and remains suspended as the foaming agent is diluted and aerated. Alternative respiratory irritants may share all of or many of these characteristics and include ground horseradish and powdered elemental sulphur. These specific alternatives are effective but less so than the ground mustard.

The respiratory irritant may also be one of various known toxic substances which may be absorbed through the respiratory tract and lungs. These poisons may cause death by avenues other than asphyxiation but are introduced to the rodent because the rodent inhales the foam. However, these toxic substances are not preferred because of the potential danger to humans, potential damage to other desirable species and other disadvantages.

In the preferred embodiment, a concentrated composition is made by mixing the foaming agent in liquid concentrate form with the mustard powder, preferably in an approximate 3:1 ratio by weight, with the goal of achieving a 1% (w:v) foaming agent concentration and approximately 0.3% to 0.5% (w:v) mustard concentration when the concentrate is diluted to a use level. The proprietary concentrated foaming agents have specific gravities of approximately 1.029 kg per liter and it is generally recommended by the respective manufacturers that it be used in 0.1% to 1% concentration. Decreasing the proportion of mustard does decrease the effectiveness of the treatment; however, a final concentration of approximately 0.3% is still effective. Increasing the proportion of mustard beyond 0.5% ratio does not appear to significantly increase the effectiveness of the composition and is therefore is not preferred.

To facilitate mixing of the mustard powder into the foaming agent, the mustard is screened to a 200 mesh to remove larger particles or clumps of powder. This screening step is not essential but is preferred.

The concentrated aqueous mixture of foaming agent and mustard is then added to sufficient water to dilute the foaming agent to about 1% and the mustard to 0.5%. It is important to add the foaming agent to the water and not the other way around to prevent premature foaming of the composition. The diluted mixture or field solution may then be stirred, taking care to prevent aeration which will cause foaming. The mixture is then pumped through an aerating nozzle to create the foam with the mustard powder suspended or slightly dissolved throughout the foam. The foam is directed into the animal burrow until the burrow is completely filled with the foam.

Pocket gophers fare known to create internal plugs in their burrows. Therefore, in some cases, it may be necessary to blow out the internal plug by pressurizing the burrow at the same time as the foam is introduced to the burrow. This may be accomplished by inserting the aerating nozzle into the burrow and packing dirt around the nozzle to block the burrow opening while inserting the foam.

The method of the present invention may readily be adapted to control rodents resident in any type of enclosed space with a limited opening such as ground burrows.

The following example is demonstrative of the invention but is not intended to be limiting of the scope of the invention.

EXAMPLES

One litre of concentrated Fire-Trol® FireFoam® manufactured and supplied by Chemonics Industries (Canada) Ltd. was mixed with 1250 mL (approximately 430 g) of ordinary white mustard powder obtained from a bulk food supplier. The mustard powder was sieved through a 200 mesh screen prior to mixing. This mixture was made up to four litres with ordinary tap water to form a concentrate. This concentrate was added to 96 litres of water to make up a full 100 litres of field solution and gently stirred.

The field solution was then sprayed through an aerating nozzle under a pressure of approximately 20 to 30 p.s.i. into live gopher burrows of two separate plots of land. At approximately 20 p.s.i., one litre of field solution produces approximately 5 litres of foam. Higher pressures will increase the volume of foam created. One plot was a 7500 square meter range pasture area while the other was a 1250 square meter alfalfa field. In all, 303 live burrows were treated and, on average, each burrow took approximately 15 seconds of treatment. After treatment, the entrance to each burrow was filled with dirt and the burrows were monitored over the next 72 hours for evidence of gopher activity. After 24 hours, only three burrows remained active and corresponded to badger (*Taxidea taxus*) holes as opposed to ground squirrel holes. Burrow activity was monitored, both before and after treatment, by shovelling dirt into the burrow opening and looking for re-excavation, indicating burrowing activity in that hole.

In laboratory testing, it was found that ground squirrels exposed to the foam/mustard combination of the preferred embodiment became inactive after 15 to 60 seconds of exposure and less than 30 seconds in most cases. There were no signs of life within 2 minutes in most cases. Following death, the respiratory tracts of the ground squirrels were examined and foam was found in the trachea and lungs of the ground squirrels. The cause of death was found to be anoxia.

In laboratory testing on Norway rats, it was found that rats submerged in the foam/mustard combination of the preferred embodiment became lethargic within 121 seconds (plus/minus 15 seconds) on average and all rats were irreversibly unconscious within 3 minutes of submersion. Mean time to loss of cardiac activity was 282 seconds (plus/minus 46 seconds). All animals became agitated upon submersion in the foam, however, movement ceased in approximately 2 minutes in most cases, the animals became lethargic, which was followed closely by unconsciousness. The foam was found in the respiratory tract of all animals and the cause of death was found to be anoxia.

In laboratory testing on pocket gophers, all animals became lethargic between 10 to 66 seconds following submersion with the average being 28 seconds. Average times to loss of consciousness and loss of cardiac activity were 79 seconds and 175 seconds respectively. All animals were found to have foam in their lungs and trachea, however, the amount of foam present varied greatly. The cause of death was found to be anoxia.

Those skilled in the art will readily appreciate that many modifications may be made to the arrangement of the present invention without departing from the scope of the invention.

The invention claimed is:

1. A rodenticidal composition comprising a suspension of ground mustard seed in an aqueous solution of a foaming agent comprising a sulfonic acid or a sulfonate.

2. The rodenticidal composition of claim 1 wherein the foaming agent comprises an alkylsulfonic acid or an olefin sulfonate.

3. The rodenticidal composition of claim 1 consisting essentially of ground mustard seed and an aqueous solution of a sulfonic acid or a sulfonate.

4. The rodenticidal composition of claim 3 wherein the sulfonic acid or a sulfonate is a salt of an alkylsulfonic acid, or a salt of an alpha-olefin sulfonate.

5. The rodenticidal composition of claim 1 wherein the foaming agent is orally non-toxic in rats.

6. The rodenticidal composition of claim 1 formed by first mixing a concentrated solution of a foaming agent with ground mustard seed, and then diluting with water to form a field solution.

7. A rodenticidal non-persistent foam comprising ground mustard seed and a foaming agent comprising an aqueous solution of a sulfonic acid or a sulfonate.

8. The foam of claim 7 wherein the foaming agent is orally non-toxic in rats.

9. The foam of claim 7 consisting essentially of ground mustard seed and an aqueous solution of a sulfonic acid or a sulfonate.

10. A rodenticidal composition comprising a suspension of ground mustard seed in an aqueous solution of a foaming agent comprising an alpha-olefin sulfonate or a salt of an alkylsulfonic acid.

* * * * *